United States Patent [19]

Cattin

[11] Patent Number: 4,536,156

[45] Date of Patent: Aug. 20, 1985

[54] INSTRUMENT FOR THE TREATMENT OF DENTAL CANALS

[75] Inventor: Francois Cattin, La Chaux-de-Fonds, Switzerland

[73] Assignee: Fluckiger & Huguenin S.A., La Chaux de Fonds, Switzerland

[21] Appl. No.: 176,333

[22] Filed: Aug. 8, 1980

[30] Foreign Application Priority Data

Sep. 26, 1979 [CH] Switzerland .................. 8659/79

[51] Int. Cl.³ .............................................. A61C 5/02
[52] U.S. Cl. ...................................... 433/102; 433/165
[58] Field of Search ................. 433/102, 105, 134; 279/102, 103, 1 Q, 23; 408/7, 710; 192/54, 55, 56 R

[56] References Cited

U.S. PATENT DOCUMENTS

| 783,856 | 2/1905 | Chaffin | 433/125 |
|---|---|---|---|
| 2,182,627 | 12/1939 | Gauld | 192/56 R |
| 2,879,069 | 3/1959 | Swanson | 279/103 |
| 3,472,045 | 10/1969 | Nelson et al. | 433/125 |
| 4,145,061 | 3/1979 | Schneider | 279/102 |

FOREIGN PATENT DOCUMENTS 640883  6/1928  France ............................... 433/102

*Primary Examiner*—Robert Peshock
*Attorney, Agent, or Firm*—Robert E. Burns; Emmanuel J. Lobato; Bruce L. Adams

[57] ABSTRACT

An instrument for use in the treatment of dental canals. The instrument includes a tool such as a pulp-burr or reamer connected by a friction coupling or slip-clutch to a mandrel driven by power to rotate the tool. Should the tool jam in a dental canal, the clutch allows the mandrel to rotate by slipping relatively to the tool thus avoiding application of excessive torque to the tool which might break it. The slip-clutch can be a helical spring fast with one end of the tool and fitted in a cylindrical bore in and co-axial with the mandrel, the spring being stressed so some of its turns press against inner surfaces of the bore to provide the friction coupling between the spring and bore.

11 Claims, 31 Drawing Figures

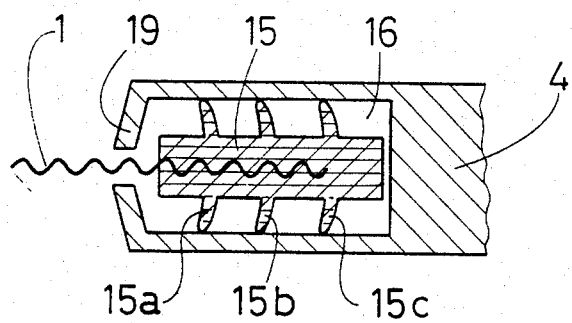
*Fig.11*
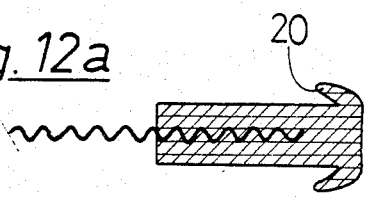
*Fig.12a*  *Fig.12b*
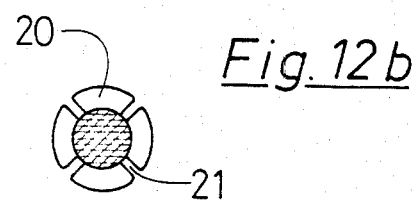
*Fig.13a*  *Fig.13b*
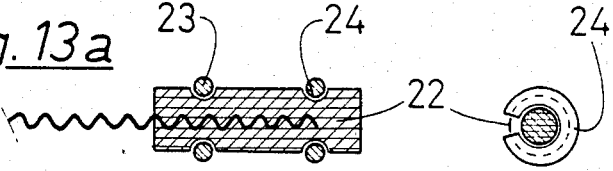
*Fig.14a*  *Fig.14b*
*Fig.15*
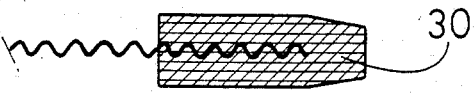

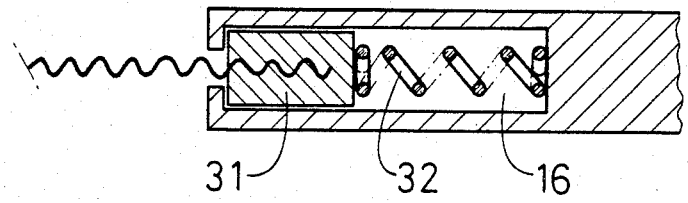
_Fig.16_
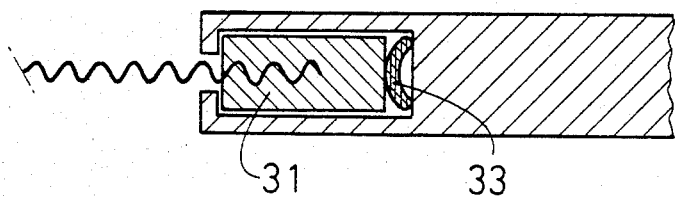
_Fig.17_
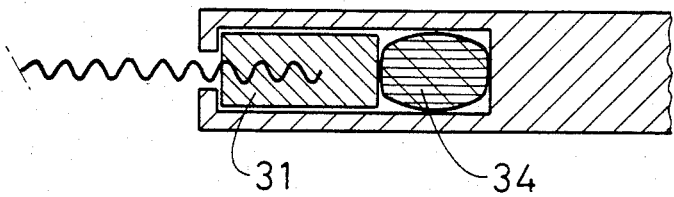
_Fig.18_
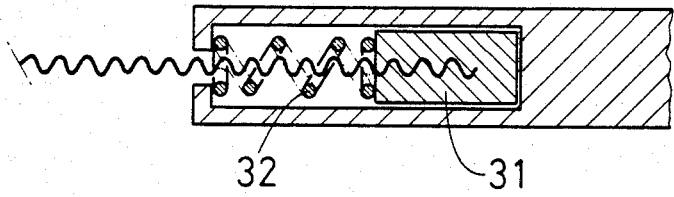
_Fig.19_

INSTRUMENT FOR THE TREATMENT OF DENTAL CANALS

BACKGROUND OF THE INVENTION

This invention relates to an instrument for the treatment of dental canals, the instrument comprising a tool fitted to a mandrel intended to be fixed to a rotary driving device. The invention relates in particular, but not exclusively, to a pulp-burr.

Pulp-burrs known hitherto are formed with an active part, herein called the tool constituted by, comprised of a helical wire fixed rigidly to a mandrel intended to be fitted to an arm to drivingly rotate the mandrel and wire. This drive is provided by a motor having a driving torque which is disproportionate with respect to the mechanical strength of the wire comprising the pulp-burr, the diameter, or thickness of the wire being frequently of the order of only several hundredths of a millimeter. Consequently this means that jamming of the pulp-burr immediately causes the wore comprising the tool to break.

Various factors may cause the sudden breakage of the pulp-burr or abnormal fatigue of the tool. Included amongst these factors are mainly: severe jamming of the end of the wire at the bottom of the canal, causing immediate breakage; slight jamming or jamming of very short but repeated duration, caused by the reciprocating movement of the instrument imparted by the operator and causing abnormal fatigue of the pulp-burr; very accentuated curvature of the end of the dental canal causing abnormal fatigue of the pulp-burr; use of an over-size pulp-burr with respect to the bore of the dental canal, causing breakage or abnormal fatigue; accidental or non-accidental placing of a head of the arm in an off-centre position with respect to the assumed axis of the canal.

The breakage of a pulp-burr or any other instrument for treating dental canals constitutes an incident which is frequently much more unpleasant than simply losing an instrument. Because not only does its replacement constitute a waste of time, but it is frequently necessary and sometimes difficult to extract that part of the instrument jammed in the dental canal.

SUMMARY OF THE INVENTION

An object of the invention, is to provide an instrument capable of being constructed so that the aforesaid drawbacks are eliminated or at least mitigated.

According to the invention there is provided an instrument for the treatment of dental canals comprising a tool fitted to a mandrel intended to be fixed to a rotary driving device, and means for transmitting by friction rotary drive between the mandrel and the tool, said drive transmitting means constituting a torquelimiting arrangement.

In one embodiment of the invention, relating to a pulp-burr, the drive transmitting means comprises a helical extension of the wire of the pulp-burr, said extension being fitted in a substantially cylindrical bore in the mandrel, said bore extending axially of the mandrel, and the extension being fitted under stress in the bore to produce a frictional connection between the extension and housing walls defining the bore.

BRIEF DESCRIPTION OF THE DRAWINGS

The invention will now be further described, by way of example, with reference to the accompanying drawings in which:

FIG. 11 shows a second embodiment of a pulp-burr formed according to the invention;

FIGS. 12 to 19 show modifications of said second embodiment;

DETAILED DESCRIPTION OF THE INVENTION

Figure 1A:
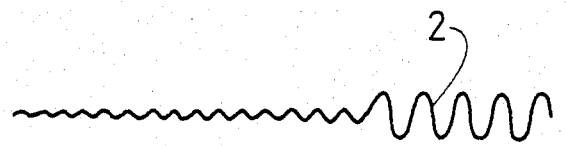
FIGS. 1a to 1c and 5, together show a first embodiment and components of a pulp-burr formed according to the invention and stages in its manufacture.
Figure 1B:
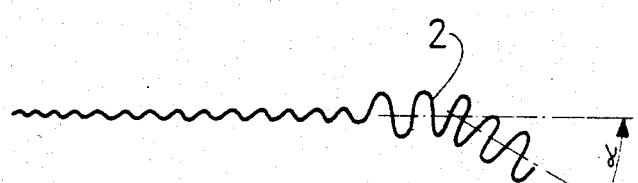
Figure 1C:
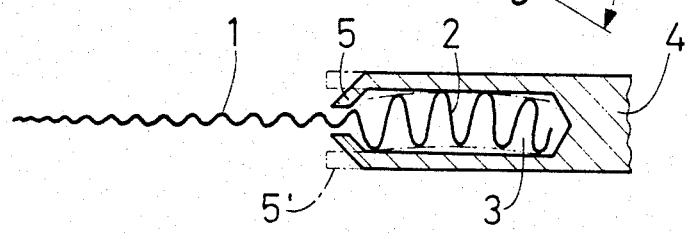
Figure 4A:
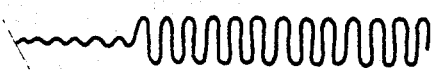
Figure 4B:
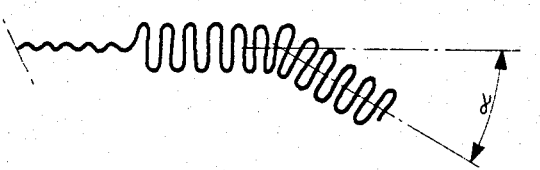
Figure 5:
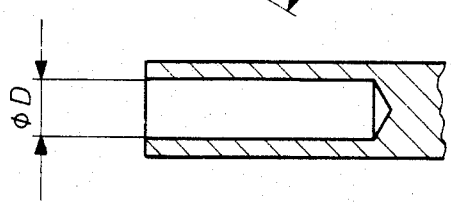

The pulp-burr illustrated in FIG. 1c comprises a tool 1 of conventional shape, i.e. comprised of a conical or cylindrical wire forming a helix which is itself conical or cylindrical. This wire 1 has an extension 2 also wound in the form of a cylindrical helix, housed in a cylindrical bore or caviity 3 in a mandrel 4, the bore extending axially of the mandrel. As shown in FIG. 1c the part 2 is supported against one side of the bore 3 by its central turns, whereas its end turns are supported against the opposite side of the bore 3. This support takes place with a pressure such that the frictional forces are sufficient to connect the tool 1 and the mandrel 4 for the purpose of rotating the tool with the mandrel under normal operating conditions. This pressure on the wall of the bore 3 is obtained in a particularly simple manner. First of all, a cylindrical helix 2 is formed as illustrated in FIG. 1a, of diameter less than the internal diameter $\phi D$ (FIG. 5) of the bore 3, the length of the helix 2 being slightly less than the length of the housing. A permanent deformation is then imparted to the helix 2 by forming a bend through a certain angle $\alpha$ (FIG. 1b), so that at least part of the helix 2 is bent at that angle relative to the axis of the tool. It is then sufficient to introduce the part 2 into the bore 3 of the mandrel, the inlet of which initially has the inner diameter of the housing, as shown in dot dash line at 5' and in FIG. 5. Then the bore is partly closed by crimping in order to form a rim 5 retaining the part 2 in the housing. At the time of the introduction of the part 2 into the bore 3, the bent part 2 is straightened under stress thus ensuring friction as described above. The value of the angle $\alpha$ determines the frictional force necessary for the correct operation of the instrument. The turns of the part 2 may be stretched apart as illustrated in FIGS. 1a to 1c or be close together side by side as illustrated in FIGS. 4a and 4b.

Figure 2:
FIGS. 2 to 4b and 6 to 8 illustrate variations of this first embodiment.
Figure 3:
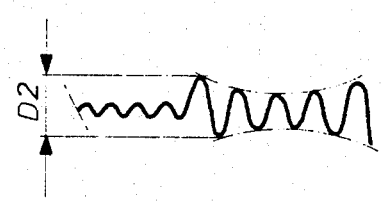

The pressure of the part 2 on the walls of the bore may be obtained by other means. For example, in FIG. 2, the helical extension has substantially the shape of an ellipsoid or barrel of which the maximum diameter D1 of the envelope defined by the ellipsoid is greater than the internal diameter of the bore 3. In the variation illustrated in FIG. 3, the helical extension defines an envelope having substantially the shape of a hyperboloid with one nappe, a maximum diameter D2 of this envelope being greater than the internal diameter of the bore 3. These tools are force-fitted in the bore of the mandrel which is closed by crimping, as described previously, or by any other means.

Figure 6:
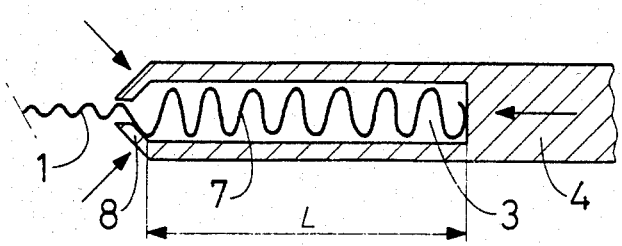

Instead of providing radial friction, it is possible to use axial friction such as in the embodiment in FIG. 6 in which the wire 1 is also extended by a cylindrical helical part 7, the diameter of which is less than the internal diameter of the bore 3. The length of the part 7 is greater than the length of the bore, so that the part 7 is compressed axially between the blind end or bottom of the bore and an edge 8 of the bore. The edge 8 is formed by crimping. The first and last turns of the part 7 frictionally engage the edge 8 and the bottom of the bore.

Figure 7:
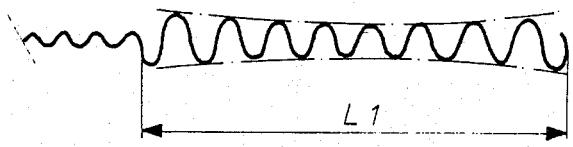
Figure 8:
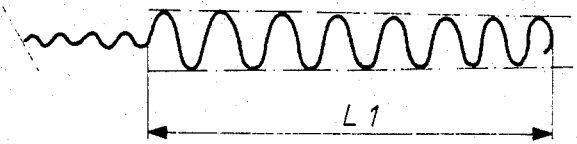

Instead of being cylindrical, the part 7 may have a variable diameter (FIG. 7) or may be of conical shape (FIG. 8), the length L1 still being greater than the length L of the bore.

A closed bore 3 may be obtained by means other than crimping. For example, in FIG. 9, the bore is formed in a tubular extension 9 of the mandrel, and is closed by a cover 10, in the form of a sleeve comprising metal or synthetic material driven onto the tube 9.

Figure 9:
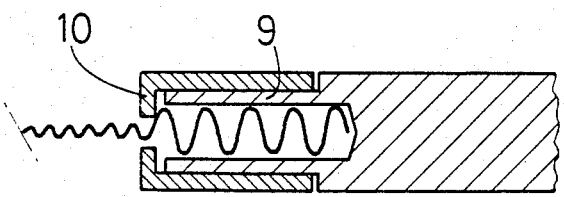
FIG. 9 shows an alternative manner of closing the bore in the mandrel.
Figure 10:
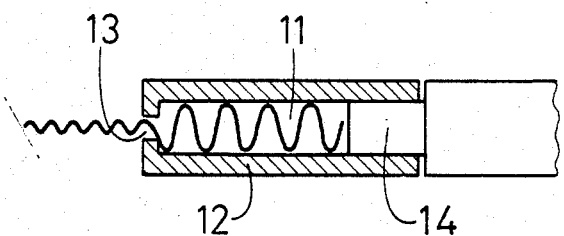
FIG. 10 shows another manner of closing the bore.

In the embodiment in FIG. 10, the bore 11 is formed by a metal sleeve 12 provided with an orifice 13 for the passage of the tool, the sleeve being driven onto a reduced diameter cylindrical part 14 of the mandrel. These two methods of assembly shown in FIGS. 9 and 10 may also be used when the tools are as shown in FIGS. 1a, 1b, 2, 3, 4a and 4b, 7 or 8. However, the methods are particularly advantageous in the case of axial compression, since they make it possible to obtain the desired compression automatically.

FIG. 11 shows an embodiment of a pulp-burr in which the rear part of the helical wire 1 is embedded in an auxiliary part 15 of cylindrical shape preferably but not necessarily formed of plastics material. The part 15 is provided with three annular flanges 15a, 15b and 15c pressing, with a certain elastic deformation of the flanges, against the wall of a cylindrical bore 16 in the mandrel 4. The bore 16 is closed by crimping 19 to form a housing retaining the auxiliary part 15 axially, which parts acts as a friction member for the rotary connection between the mandrel 4 and tool 1.

In the modification in FIGS. 12a and 12b the radial friction is ensured by a single flange 20 provided with slots 21.

In FIGS. 13a and 13b, the auxiliary part is formed by a cylinder 22 having two annular grooves in which are fitted two split rings 23 and 24 of which the outer diameter is greater than the internal diameter of the bore 16.

In FIGS. 14a and 14b, the auxiliary part is formed by a cylinder 25 provided with four flexible longitudinal ribs 26, 27, 28 and 29.

In FIG. 15, the auxiliary part 30 is formed by a cylindrical block having a frustoconical end. This block is of resilient material and the diameter of the block is slightly greater than the internal diameter of the bore 16.

In the modifications in FIGS. 16 to 19, the auxiliary part is comprised of a simple cylinder 31 having a diameter less than the internal diameter of the bore 16. Axially directed pressure against one of the ends of the bore is provided by a coil spring 32 which is under compression in the bottom of the bore (FIG. 16), or at the open end of the bore (FIG. 19), or by a curved washer 33 which is independent of or integral with the part 31 (FIG. 17), or by a resilient buffer 34 of rubber or other material compressed at the bottom of the bore (FIG. 18).

Instead of being closed by crimping as illustrated in FIGS. 16 to 19, the bore may be closed by any other means, in particular those illustrated in FIGS. 9 and 10.

Figure 20:
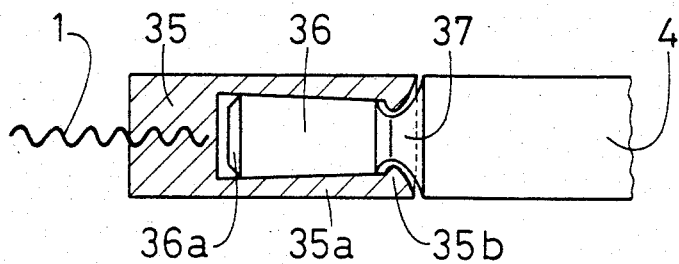
FIG. 20 shows a third embodiment of a pulp-burr formed according to the invention.

In the embodiment illustrated in FIG. 20, the tool 1 is embedded in an auxiliary part 35 comprising a tubular extension 35a which is conical at its inside and longitudinally or otherwise split. The extension 35a surrounds a conical extension 36 of the mandrel of similar shape to the interior of the part 35a. The auxiliary part 35 has a rib 35b engaging a groove 37 in the mandrel to retain the auxiliary part. The part 36 has a frustoconical end 36a facilitating the forcefitting of the part 35 on the mandrel. The part 35 may be of metal or synthetic material.

Figure 21:
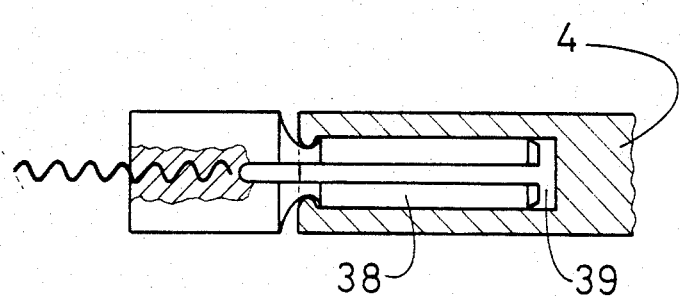
FIGS. 21 to 23 show modifications of said third embodiment.

FIG. 21 shows a modification in which the auxiliary part is provided with an end-piece 38 which is split longitudinally and introduced by elastic deformation into a bore 39 in the mandrel 4.

Figure 22:
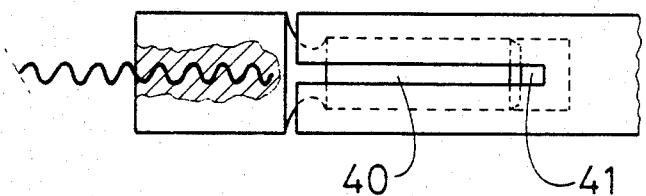

FIG. 22 shows a modification in which the auxiliary part comprises a cylindrical end-piece 40 force-fitted in a bore in the mandrel formed with one or more slots 41 extending longitudinally of the mandrel to facilitate radial elastic deformation of the housing.

Figure 23:
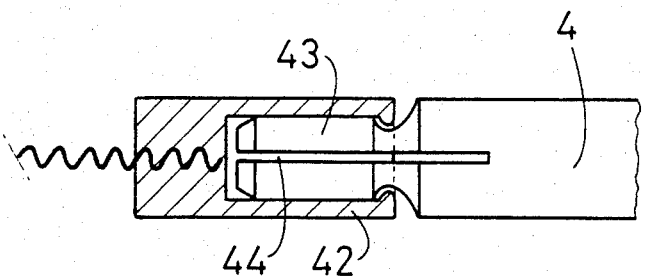

In FIG. 23 the auxiliary part comprises a tubular extension which is not split and in which is introduced an end-piece 43 of the mandrel formed with a slot 44 facilitating radial elastic deformation of the end-piece 43 upon its introduction under stress into the part 42.

The invention is not limited in its application to pulp-burrs, but extends to all instruments for dental canals, for example to instruments intended for drilling dental canals, whether driven manually or mechanically. The driving connection between the tool and mandrel may be produced, for example, by one of the methods illustrated in FIGS. 11 to 23 or by other methods as illustrated, for example, in FIGS. 24 and 25.

Figure 24:
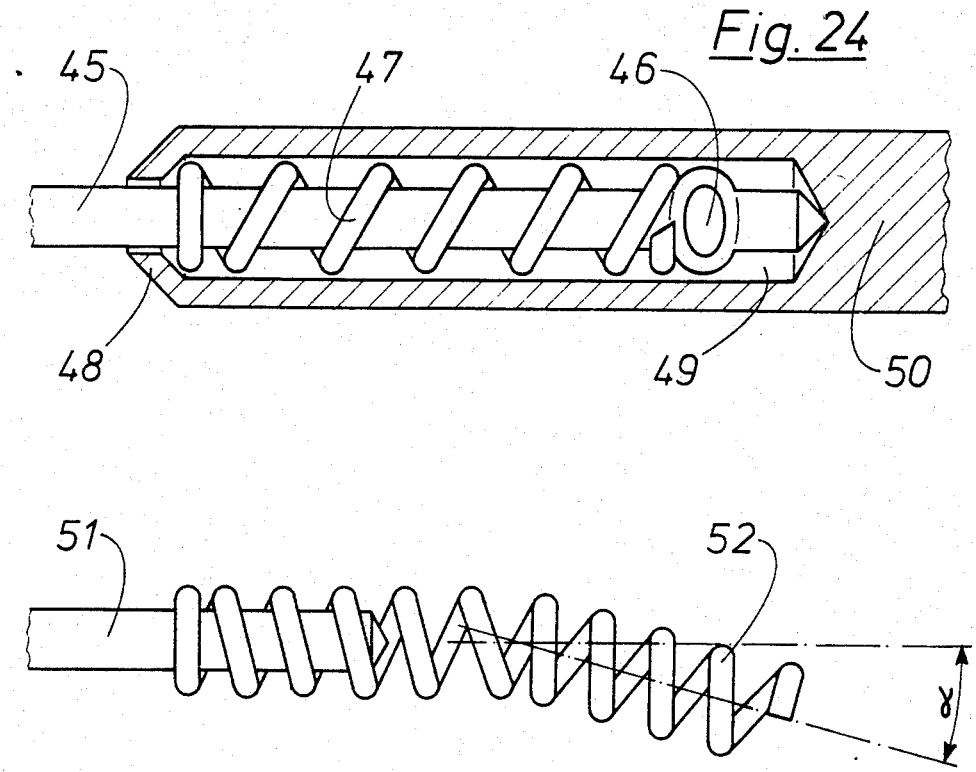
FIG. 24 shows a fragment of a reamer formed according to the invention.

In FIG. 24, the tool proper, for example a reamer (not shown), has a shank 45 formed with a stop 46 produced by compression. One end of spring 47 presses against the stop and the other end presses against a bent or turned in edge 48 of a bore 49 in the mandrel 50. A rear end of the tool is thus pressed against the bottom of the bore 49. The inner diameter of the spring 47 is greater than the diameter of the shank 45.

Figure 25:
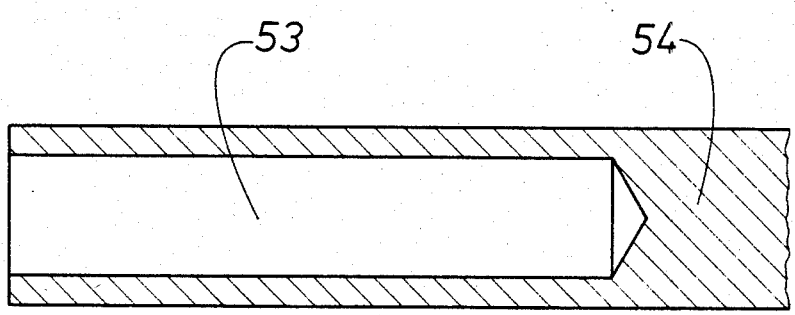
FIG. 25 shows fragments of components of another embodiment of a reamer formed according to the invention.

In the embodiment illustrated in FIG. 25, a shank 51 of a tool, for example a reamer, is fixed in the end of a spring 52 in a manner preventing relative rotation between the shank and the part of the spring fixed thereto. In the unstressed state the spring is bent at angle $\alpha$ to the axis of the shank and it is straightened under stress when the spring is introduced into the bore 53 in the mandrel 54. The frictional rotary drive takes place in the same manner as in the example shown in FIGS. 1a to 1c.

What is claimed is:

1. An instrument for the treatment of dental canals comprising: a mandrel having a substantially cylindrical bore extending axially of said mandrel; and a pulp burr comprising a helical wire having a helical extension fitted in the substantially cylindrical bore under stress, the cylindrical bore and the helical extension fitted in the cylindrical bore under stress together comprising drive transmitting means having a torque-limiting function for transmitting rotation of the mandrel by friction to the pulp-burr wherein said extension is of substantially cylindrical helical form which prior to being fitted under stress in the cylindrical bore is bent at an angle to the axis of the helical pulp-burr.

2. An instrument as claimed in claim 1, in which the extension is a helix having an envelope substantially in the shape of an ellipsoid, a maximum diameter of the extension in an unstressed state prior to insertion in the bore being greater than the internal diameter of the bore.

3. An instrument as claimed in claim 1, in which the extension is a helix having an envelope substantially in the form of a hyperboloid with one nappe, a maximum diameter of the extension in an unstressed state prior to insertion in the bore being greater than the internal diameter of the bore.

4. An instrument as claimed in claim 1, 2 or 3, in which the extension is compressed radially in the bore.

5. An instrument as claimed in claim 1, 2 or 3, in which said extension is compressed axially in the bore.

6. An instrument as claimed in claim 1 in which the rotary drive transmitting means comprises an auxiliary part fixed to the tool and friction-fitted to the mandrel.

7. An instrument as claimed in claim 6 in which a substantially cylindrical bore in the mandrel extends axially of the mandrel, and the auxiliary part in the bore is urged axially by resilient means.

8. An instrument as claimed in claim 6, in which the auxiliary part is provided with flexible fins or ribs compressed radially in a substantially cylindrical bore in the mandrel and extending axially of the mandrel.

9. An instrument as claimed in claim 6, in which the auxiliary part is provided with split rings compressed radially in a substantially cylindrical bore in the mandrel and extending axially of the mandrel.

10. An instrument as claimed in claim 6, in which the auxiliary part is in the form of a cover on one end of the mandrel, said cover having an internal shape substantially similar to the shape of said end.

11. An instrument for the treatment of dental canals comprising: a mandrel, a tool fitted to said mandrel, and drive transmitting means having a torque-limiting function for transmitting rotation of the mandrel by friction to said tool, said drive transmitting means comprising a cylindrical bore in the mandrel, said bore extending axially of the mandrel, the tool having a shank fixed to an end of a coil spring, said spring being disposed under stress in the bore, and prior to said spring being disposed in the bore the spring being bent at an angle to the axis of the shank.

* * * * *